United States Patent
Ho Ba Tho et al.

(10) Patent No.: US 8,506,644 B1
(45) Date of Patent: Aug. 13, 2013

(54) ACETABULAR PROSTHESIS TO BE FIXED WITHOUT CEMENT

(75) Inventors: Marie-Christine Ho Ba Tho, Compiegne (FR); François Roux, Paris (FR); Maximilien Vanleene, Wasquehal (FR)

(73) Assignees: Centre National de la Recherche Scientifique (CNRS), Paris (FR); Universite Technologie de Compiegne—UTC, Compiegne Cedex (FR)

( * ) Notice: Subject to any disclaimer, the term of this patent is extended or adjusted under 35 U.S.C. 154(b) by 330 days.

(21) Appl. No.: 11/667,278

(22) PCT Filed: Nov. 8, 2005

(86) PCT No.: PCT/EP2005/055810
§ 371 (c)(1),
(2), (4) Date: Nov. 8, 2007

(87) PCT Pub. No.: WO2006/048461
PCT Pub. Date: May 11, 2006

(30) Foreign Application Priority Data

Nov. 8, 2004 (FR) ..................... 04 11865

(51) Int. Cl.
*A61F 2/32* (2006.01)
(52) U.S. Cl.
USPC .................. 623/22.38; 623/22.32; 623/22.21
(58) Field of Classification Search
USPC .......... 623/22.21, 22.23, 22.27, 22.31, 22.32, 623/22.38
See application file for complete search history.

(56) References Cited

U.S. PATENT DOCUMENTS

| | | | | |
|---|---|---|---|---|
| 3,903,549 A | * | 9/1975 | Deyerle | 623/22.36 |
| 4,878,918 A | * | 11/1989 | Tari et al. | 623/22.35 |
| 6,290,726 B1 | * | 9/2001 | Pope et al. | 623/22.15 |
| 6,582,470 B1 | * | 6/2003 | Lee et al. | 623/23.55 |
| 6,626,949 B1 | | 9/2003 | Townley | |

FOREIGN PATENT DOCUMENTS

| | | |
|---|---|---|
| DE | 3630276 | 3/1988 |
| DE | 19731442 | 2/1999 |
| DE | 19915814 | 10/2000 |
| EP | 0963740 | 12/1999 |
| EP | 1068843 | 1/2001 |
| FR | 2551655 | 3/1985 |
| FR | 2641461 | 7/1990 |
| FR | 2715556 | 8/1995 |
| FR | 2788685 | 7/2000 |
| GB | 2351671 | 1/2001 |
| WO | WO-96-04862 | 2/1996 |
| WO | WO-01-35873 | 5/2001 |

* cited by examiner

*Primary Examiner* — David Isabella
*Assistant Examiner* — Joshua Levine
(74) *Attorney, Agent, or Firm* — Blakely, Sokoloff, Taylor & Zafman

(57) ABSTRACT

The invention relates to an acetabular prosthesis comprising an, in general, hemispherically shaped insert (1) having a crown (5) and an apex (4), this insert being provided, on its outer surface (2), with at least one fin. The invention is characterized in that the fin (6) has a face (9) starting from the crown (5) of the insert (1) and extending toward the apex (4) of the insert while forming a crest (10). This crest (10) has an, in particular, curved shape.

16 Claims, 2 Drawing Sheets

ACETABULAR PROSTHESIS TO BE FIXED WITHOUT CEMENT

Figure 1:
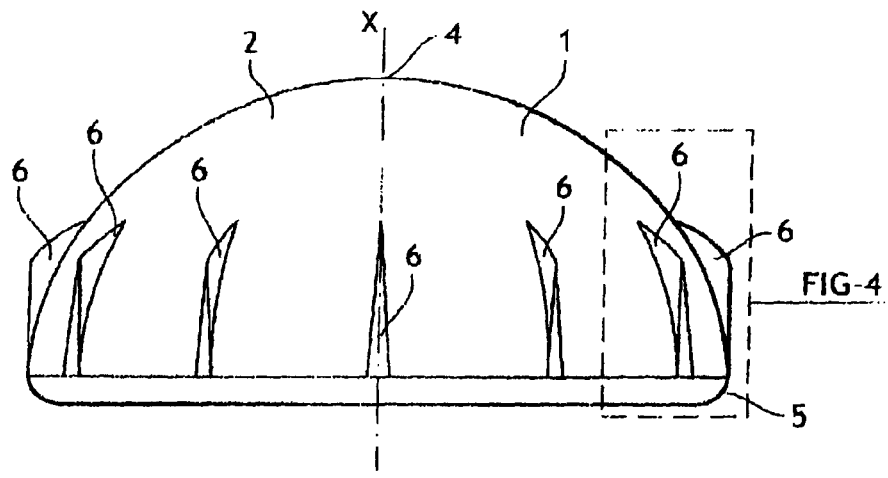

The present patent application is a non-provisional application claiming the benefit of International Application No. PCT/EP2005/055810, filed Nov. 8, 2005.

The invention relates to the field of acetabular prostheses to be fixed without cement.

Hip arthroplasty is a surgical operation which consists of replacing the joint of the hip by an artificial joint called a "total hip prosthesis". The total hip prosthesis comprises a femoral prosthesis to be fixed in the femur on the one hand, the femoral prosthesis comprising a stem provided with a femoral head, and an acetabular prosthesis (or acetabulum) to fixed in the acetabular cavity of the pelvis bone on the other hand, the acetabular prosthesis having a cavity for receiving the femoral head of the femoral prosthesis.

There are presently several techniques for fixing acetabular prostheses.

According to certain techniques, the acetabular prosthesis is fixed in the bone by means of cement, generally based on PolyMethylMethAcrylate (PMMA). This technique leads to good medium and long term results. However, aseptic loosening of the prosthesis in the long term is routinely reported.

According to other techniques, the acetabular prosthesis is fixed in the bone without any cement by mechanical means. By fixing it without any cement, it should be able to obtain in the first months after implantation, effective mechanical strength of the prosthesis in the bone in order to promote osteointegration, i.e., integration of the prosthesis to the bone tissues. The cement-less prostheses used generally consist of a metal cup and of a PolyEthylene (PE) insert placed in the metal cup. Fixing the metal cup in the bone may be achieved by different fixing means. These fixing means may notably comprise screws, pads, fins, or pins. Further, the acetabular prosthesis may be fixed in the bone cavity by forced insertion (or press-fit) so that the prosthesis is held tight in the bone cavity.

Document FR 2 641 641 (published on Jul. 13, 1990) describes an acetabular prosthesis which may be used without any cement, comprising a hemispherical cap provided on its perimeter with a series of fins uniformly positioned over the convex surface of the cap and a covering component intended to be applied by engagement on the concave surface of the cap. The fins have the shape of wedges, the apices of which are turned towards the apex of the cap.

This document indicates that the fins are designed in order to be forcibly engaged into the bone housing, so as to thereby define an engagement by insertion associated with a bone compression effect which directly depends on the wedge shape of the fins.

The thereby positioned fins substantially act on the edge of the acetabulum area, i.e., where the bone is very compact and may therefore withstand the exerted forces because of this.

The problem which the invention proposes to solve is to provide an acetabular prosthesis to be fixed in a bone cavity without any cement, having good mechanical strength in the bone cavity while avoiding deterioration of the bone in contact with the prosthesis.

This problem is solved within the scope of the present invention, by means of an acetabular prosthesis comprising an insert with a general hemispherical shape, having an edge and an apex, the insert being provided on its outer surface with at least one fin, characterized in that the fin has a facet extending from the edge of the insert and extending towards the apex of the insert while forming a crest, the crest having a substantially curved shape.

The facet of the fin is intended to be supported on the cortical bone without damaging the bone tissue. With the facet, it is possible to distribute the stresses exerted by the insert over the cortical bone.

With the curved shape of the crest of the fin, the prosthesis may be anchored in the cancellous bone while also avoiding any damage of the bone tissue.

The fin(s) provide(s) mechanical strength of the prosthesis in the bone until osteointegration is sufficient to take over. In particular, the fins hold the insert in position during movement of the femoral head.

The prosthesis may have the following features:
the facet of the fin extends adjacent to the outer surface of the insert at the crown of the insert,
the fin has two edges delimiting the facet, both edges each extending from the crown of the insert and joining together at the crest,
the facet has a general triangular shape,
the facet extends along a cylindrical surface with as axis, the axis of the insert,
the crest has a convex shape curved towards the apex of the insert,
the crest extends in a radial plane of the insert,
the prosthesis comprises a plurality of identical fins,
the prosthesis comprises at least 12 fins,
the fins are uniformly distributed around the crown of the insert,
the crown of the insert has a general rounded shape,
the prosthesis is formed in titanium,
the prosthesis has an internal concave surface intended to receive a femoral head, the internal surface being covered with a layer of Diamond-Like-Carbon (DLC) coating,
the prosthesis has an external convex surface intended to be in contact with the bone, the external surface being covered with a layer of hydroxyapatite coating,
the prosthesis has an external convex surface intended to be in contact with the bone, the external surface having a roughness between 2 µm and 4 µm, preferably of the order of 3 µm,
the prosthesis is formed as a single part.

Figure 2:
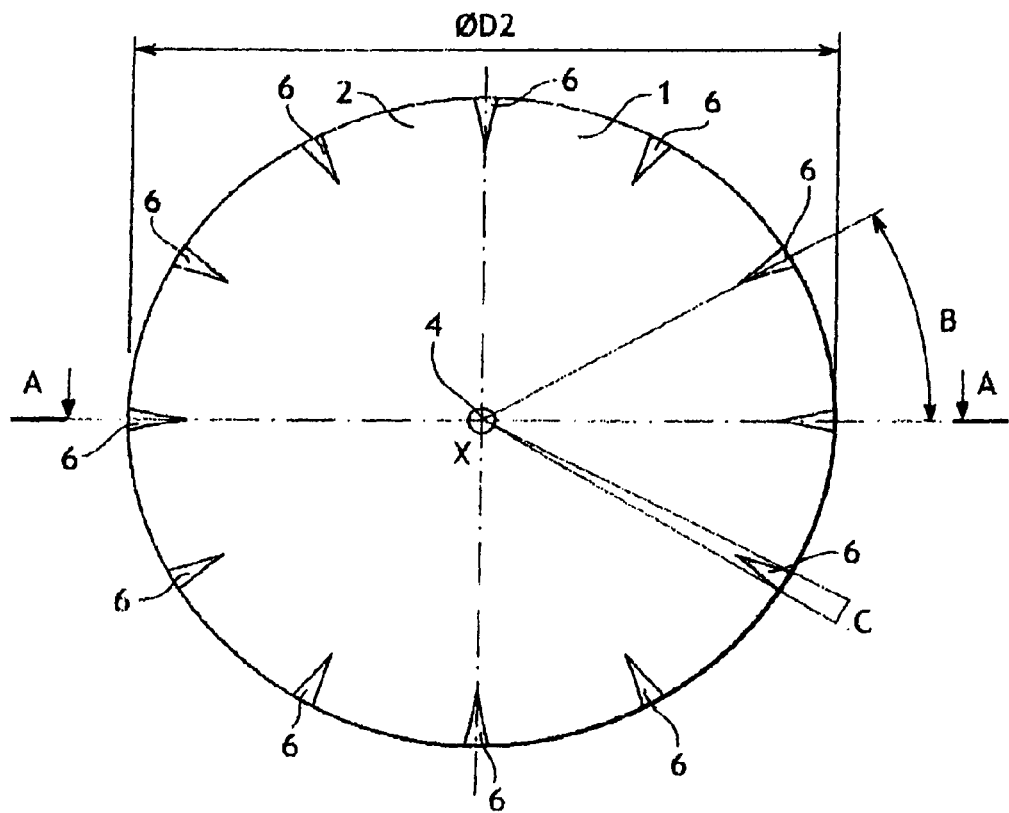
Figure 3:
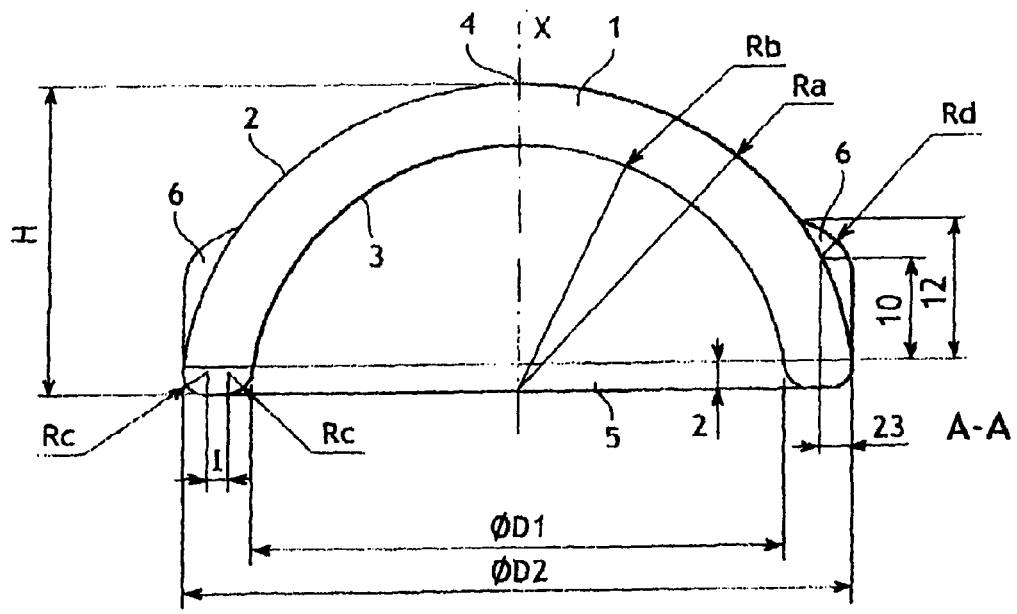
Figure 4:
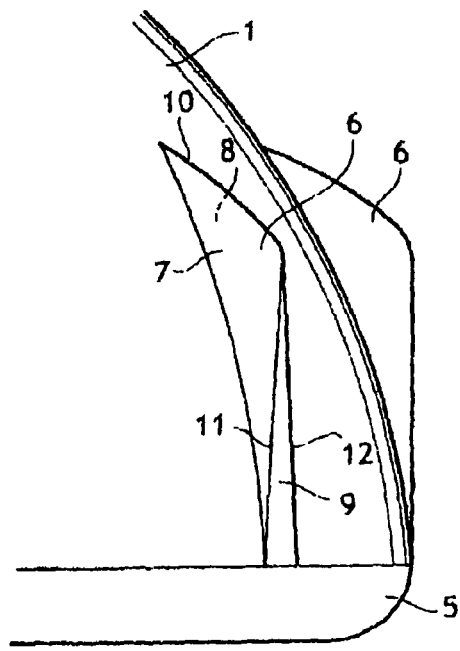

Other features and advantages will further become apparent from the description which follows, which is purely illustrative and non-limiting. The description should be read with reference to the appended figures, which illustrate an acetabular prosthesis according to a possible embodiment of the invention:

FIG. 1 schematically illustrates the acetabular prosthesis in a side view,

FIG. 2 schematically illustrates the acetabular prosthesis in a top view,

FIG. 3 schematically illustrates the acetabular prosthesis in a sectional view,

FIG. 4 schematically illustrates a fin of the acetabular prosthesis.

The acetabular prosthesis illustrated in these figures comprises an insert 1 with a general hemispherical shape. The insert 1 has an external convex surface 2 intended to be in contact with the bone of the acetabular cavity of the pelvis and an internal concave surface 3 intended to receive a femoral head.

The insert 1 has an apex 4 and a crown 5. The "apex" designates the point of intersection of the axis X of revolution of the insert 1 with the external surface 2 of the insert. The "crown" designates the edge of the insert 1 extending between the external surface 2 and the internal surface 3.

The insert 1 is provided on its external surface 2 with a plurality of identical fins 6 uniformly distributed around the crown 5.

Each fin 6 is symmetrical relatively to a radial plane of the insert 1, i.e. a plane passing through the axis of the insert (marked as X). Each fin has two side flanks 7 and 8. Each fin 6 further has a facet 9 and a crest 10 extending between the side flanks 7 and 8. The side flanks 7 and 8 extend on either side of the facet 9 and join together at the crest 10. The flanks 7 and 8 form edges 11 and 12 at their junction with the facet 9.

Each facet 9 is of a general triangular shape with an apex directed towards the apex 4 of the insert. Each facet 9 extends along a cylindrical surface with as an axis, the axis X of the insert 1. The facet 9 extends from the crown 5 of the insert 1 and extends towards the apex 4 of the insert forming the crest 10. Both edges 11 and 12 delimiting the facet 9 thereby each extend from the crown 5 and join together at the crest 10.

Each crest 8 extends in a radial plane of the insert 1. Each crest 8 has a substantially convex shape curved towards the apex 4 of the insert 1.

The facets 9 are intended to be supported against the cortical bone of the acetabular cavity, i.e., the hardest portion of the bone which is in contact with the crown 5. The shape and the positioning of the facets 9 around the crown 5 allow the stresses to be properly distributed around the crown 5, when the insert is held tight in the acetabular cavity.

The crests 10 are intended to anchor the prosthesis in the cancellous (or trabecular) bone of the acetabular cavity, i.e., the tenderest portion of the bone which is in contact with the external convex surface of the insert 1. With the curved shape of the crests 10, the insert may be anchored while avoiding any requirement for very incisive components (such as wedges for example) which may cause damages in the bone.

The peculiar shape of the fins 6 thereby allow a gradual transition between a supporting portion of the insert (formed by the facets) and an anchoring portion (formed by the crests).

Moreover, the crown 5 has a general rounded shape. With this feature, it is possible to limit luxation risks of the joint.

The insert 1 is formed as a single part, for example in titanium.

The external surface 2 of the insert 1 is treated so as to have a roughness of the order of 3 μm, and is covered with a layer of hydroxyapatite coating. These features have the purpose of facilitating colonization of the external surface of the insert 1 by bone cells and of thereby promoting osteointegration of the prosthesis.

Moreover, the internal surface 3 of the insert is covered with a layer of Diamond-Like-Carbon (DLC) coating, which is an amorphous form of carbon containing a large amount of carbon $sp^3$ hybrids which give it properties close to those of diamond.

The DLC coating improves the wear resistance properties of the internal surface intended to be in contact with the femoral head. Further, because of its chemical inertia, the biocompatibility of the DLC coating is very good.

As a non-limiting example, the prosthesis illustrated in FIGS. 1-4 has the following dimensions:

| | | |
|---|---|---|
| Internal diameter of the insert | ØD1 | 40 mm |
| External diameter of the insert | ØD2 | 50 mm |

-continued

| | | |
|---|---|---|
| Internal radius of the insert | Rb | 20 mm |
| External radius of the insert | Ra | 25 mm |
| Height of the insert | H | 25 mm |
| Radius of the crown | Rc | 2 mm |
| Height of a facet | | 10 mm |
| Height of a fin | | 12 mm |
| Radius of curvature of a crest | Rd | 2.3 mm |
| Angle between two fins | B | 30° |
| Angle occupied by a fin | C | 5° |

The invention claimed is:

1. An acetabular prosthesis consisting of an insert with a general hemispherical shape, having a crown and an apex, the insert being provided on its outer surface with at least one fin that is sharp such that the at least one fin may be anchored to a bone, the at least one fin having a crest and a base, the at least one fin having a facet extending from the crown of the insert towards the apex of the insert, two side flanks extending from the facet and the crest having a shape substantially curved towards the apex of the insert, wherein the side flanks join together at the crest.

2. The prosthesis according to claim 1, wherein the facet of the fin extends adjacent to the outer surface of the insert at the crown of the insert.

3. The prosthesis according to claim 1, wherein the fin has two edges delimiting the facet, both edges each extending from the crown of the insert and joining together at the crest.

4. The prosthesis according to claim 1, wherein the facet has a general triangular shape.

5. The prosthesis according to claim 1, wherein the facet extends along a cylindrical surface with as an axis, the axis of the insert.

6. The prosthesis according to claim 1, wherein the crest extends in a radial plane of the insert.

7. The prosthesis according to claim 1, comprising a plurality of identical fins.

8. The prosthesis according to claim 7, comprising at least 12 fins.

9. The prosthesis according to claim 7, wherein the fins are uniformly distributed around the crown of the insert.

10. The prosthesis according to claim 1, wherein the crown of the insert has a general rounded shape.

11. The prosthesis according to claim 1, formed in titanium.

12. The prosthesis according to claim 1, having an internal concave surface intended to receive a femoral head, the internal surface being covered with a layer of Diamond-Like-carbon (DLS) coating.

13. The prosthesis according to claim 1, having an external convex surface intended to be in contact with the bone, the external surface being covered with a layer of hydroxyapatite coating.

14. The prosthesis according to claim 1, having an external convex surface intended to be in contact with the bone, the external surface having a roughness between 2 μm and 4 μm, preferably of the order of 3 μm.

15. The prosthesis according to claim 1, wherein said prosthesis forms a single integral unit.

16. The prosthesis according to claim 14, wherein the roughness is approximately 3 μm.

* * * * *